United States Patent
Saladin et al.

(10) Patent No.: US 7,748,899 B2
(45) Date of Patent: Jul. 6, 2010

(54) X-RAY DEVICE

(75) Inventors: Jean Pierre Saladin, Bagneux (FR); Bernard Charpillat, Nerville la Foret (FR); Romain Chatelin, Plaisir (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/138,845

(22) Filed: Jun. 13, 2008

(65) Prior Publication Data

US 2009/0180594 A1    Jul. 16, 2009

(30) Foreign Application Priority Data

Jul. 12, 2007    (FR)    ................... 07 56464

(51) Int. Cl.
*H05G 1/02*    (2006.01)
*A61B 6/08*    (2006.01)

(52) U.S. Cl. ...................... 378/197; 378/205
(58) Field of Classification Search ......... 378/193–197, 378/205
See application file for complete search history.

(56) References Cited

U.S. PATENT DOCUMENTS

| | | | | |
|---|---|---|---|---|
| 383,286 A | * | 5/1888 | Prendergast et al. ........... 172/73 |
| 4,805,202 A | * | 2/1989 | Deucher et al. ............. 378/209 |
| 5,048,069 A | | 9/1991 | Siczek | |
| 5,050,204 A | * | 9/1991 | Siczek et al. ................ 378/197 |
| 6,325,537 B1 | * | 12/2001 | Watanabe .................... 378/197 |
| 6,428,206 B1 | | 8/2002 | Watanabe | |
| 2003/0091156 A1 | | 5/2003 | Crain et al. | |
| 2006/0256926 A1 | | 11/2006 | Hiyama | |
| 2007/0165775 A1 | | 7/2007 | Graumann | |

FOREIGN PATENT DOCUMENTS

DE    10 2005 032288    1/2007

* cited by examiner

*Primary Examiner*—Irakli Kiknadze
(74) *Attorney, Agent, or Firm*—Global Patent Operation

(57) ABSTRACT

An X-ray radiology device comprising a rotating and flat lift. For this X-ray device to operate correctly, it is necessary to obtain and maintain, for all the incidence angles, a perfect alignment of the focal point of the X-ray tube, the element observed and the detector. This geometric imperative is achieved in one embodiment by means of a compensation system. The compensation system includes a cam fitted to a free end of the lift. The compensation system includes a lever in contact with the profile of the cam. The lever is in contact with the detector or the tube connected to the lift. Thus, when the lift rotates, the cam pushes the lever, which in return pushes the tube or the detector in order to align it.

10 Claims, 1 Drawing Sheet

X-RAY DEVICE

CROSS-REFERENCE TO RELATED APPLICATIONS

This application claims priority under 35 U.S.C. §119(a)-(d) to prior-filed, co-pending French patent application serial number 0756464, filed on Jul. 12, 2007, which is hereby incorporated by reference in its entirety.

BACKGROUND

1. Field of the Invention

The field of the invention relates to medical imaging generally, and more particularly, to radiography or radioscopy or mammography.

2. Prior Art

Mobile X-ray devices are known that comprise moving parts enabling them to turn in different directions around a patient. These moving parts thereby enable a beam of X-rays to be oriented, so as to analyze a given part of the body of the patient.

These moving parts are capable of moving in the three dimensions of a space. These moving parts are composed, in general, of a cradle comprising an X-ray tube on one of its ends and a detector on another of its ends. This tube enables a beam of X-rays to be emitted along an emission direction.

The detector is coupled to the cradle on the opposite side to the tube and in the emission direction. The detector or the tube is connected to a linear lift enabling said detector or said tube to be raised and lowered vertically in the emission direction.

However, the considerable volume of the lift does not enable the moving parts of the X-ray device to occupy all of the possible positions around the patient during a radiological examination. The examination angles are thereby restricted by this volume. Similarly, the speed of the lift cannot exceed a certain threshold due to this volume.

The document U.S. Pat. No. 6,742,929 ("the '929 patent") teaches displacing the detector in a rotating manner. This displacement takes place in the plane of the detector, in other words horizontally. This document does not enable the detector or the tube to be raised or lowered vertically. Moreover, with this document, the image viewed by the practitioner is no longer suitable for the diagnosis since it comprises erroneous information. Indeed, the detector is displaced along an arc of circle. As a result, the detector is no longer perfectly aligned with the X-ray tube. The images supplied by the detector do not allow the practitioner to make a correct diagnosis.

SUMMARY OF THE INVENTION

These and other disadvantages of the prior art are addressed by embodiments of the present invention, which aim, among other things, to reduce a volume of a lift that bears either the tube or the detector of an X-ray device, while also increasing alignment accuracy of the focal point of the tube, an element observed, and the detector. Thus, a non-linear rotating lift is proposed, which does not have a horizontal movement as in the background art.

To resolve the problems of the '929 patent described above, embodiments of an X-ray device as set forth herein includes compensation means capable of positioning the detector, the focal point of the tube and the element observed in a same alignment during rotation of the lift.

The use of a rotating raising and lowering movement of the lift within the C arm enables the volume of the lift to be reduced. This reduction in the volume of the lift makes it possible to increase the positions that the moving parts of the X-ray device occupy around the patient during a radiological examination. This increases the examination angles. This rotating movement of the lift also enables the speed of the lift to be increased.

BRIEF DESCRIPTION OF THE DRAWINGS

Embodiments of the present invention may best be understood by reference to the following detailed description taken in conjunction with the accompanying drawings. These drawings are provided as an indication only and in no way limit the scope of the claimed invention. These figures show:

DETAILED DESCRIPTION OF EMBODIMENTS OF THE INVENTION

Figure 1:
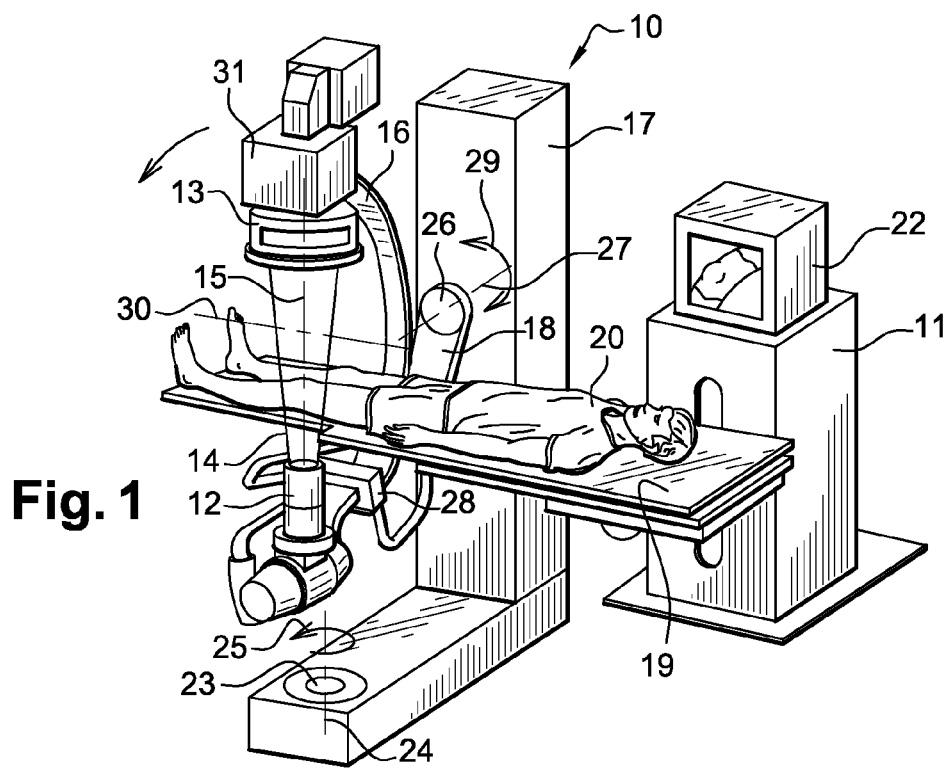
FIG. 1 illustrates a spatial representation of a vascular type of X-ray device, as set forth in an embodiment of the invention.

FIG. 1 shows a spatial representation of an X-ray device, as set forth in an embodiment of the invention. More precisely, this device 10 is a device known as a vascular type device that comprises in particular an X-ray tube 12 and an X-ray detector 13. This tube 12 emits a beam 14 of X-rays along an emission direction 15.

The tube 12 and the detector 13 are both coupled to the ends, on either side, of a C-shaped arm 16. Indeed, the detector 13 is coupled to the arm 16 opposite the tube 12 and in the emission direction 15, so as to receive the beam 14 of rays. Moreover, the arm 16 is connected to an L-shaped strut 17 with the help of an intermediate arm 18. A collimator situated inside the detector 13 may enable a shape to be given to the beam 14 of X-rays emitted by the tube 12. Thus, this collimator may in particular modify the width of the beam 14.

A bed 19 on which a patient 20 is laid out is fixed and coupled to a frame 11. This bed 19 is placed within the C-shaped arm 16, so that the tube 12 is located under the bed 19 and the detector 13 above the bed 19. Whatever the examination performed, the tube 12 and the detector 13 preferably always maintain this spatial configuration. The tube 12 may in certain examinations be located above the examination table 9 and the detector 13 underneath the examination table 9.

Under these conditions, after having received the beam 14 that passes through a part of the body of the patient, the detector 13 emits electrical signals corresponding to the intensity of the rays received. These electrical signals may then be transmitted to a computer 22 via wire connections not shown. These electrical signals can enable this computer 22 to produce an image corresponding to the part of the body analyzed. This image may be viewed by means of a screen of this computer 22 within the context of radioscopy, or printed out on a sheet within the context of radiography.

With the aim of being able to examine each part of the body of the patient 20, the beam 14 may be oriented in a multitude of directions around the patient. Indeed, the position of the tube 12 and the detector 13 may be modified by a user. To this end, the L-shaped strut 17, the intermediate arm 18 and the C-shaped arm 16 are all hinged in relation to each other.

More precisely, the L-shaped strut 17 is hinged around the ground (comparable to the fixed frame 11) through the intermediary of a first hollow motor 23. This motor 23 thereby enables the strut 17 to rotate around a vertical axis 24 in a rotation 25 (FIG. 1).

A bed 19 on which a patient 20 is laid out is fixed and coupled to a frame 11. This bed 19 is placed within the C-shaped arm 16, so that the tube 12 is located under the bed 19 and the detector 13 above the bed 19. Whatever the examination performed, the tube 12 and the detector 13 preferably always maintain this spatial configuration. The tube 12 may in certain examinations be located above the examination table 19 and the detector 13 underneath the examination table 19.

As regards the C-shaped arm 16, it can slide around a link 28. The arm 16 may thereby turn around an axis 30 that passes through the centre of a disc described by two arms in C placed side by side. This axis 30 is moreover perpendicular to the axis 27 and the axis 24 for the position represented.

By combining the rotational movements around the three axes 24, 27 and 30, the beam 14 of X-rays can describe all the emission directions of the X-rays included within a sphere. Thanks to the motors 23 and 26 and the link 28, the beam 14 can thereby pass through each part of the patient along a multitude of possible orientations.

The detector 13 is connected to an end of a lift 31 enabling said detector 13 to be raised and lowered in the emission direction 14. The lift 31 is connected to the arm 16. The X-ray device comprises a motorization (not shown) with a first point fixed to the C-shaped arm 16 and a second point fixed to the lift 31 enabling said lift to have a rotating movement.

This motorization is obtained by an electric motor or by gear assemblies.

The X-ray device 10 is here of vascular type, although it may be of mammographic or radioscopic or other type. The vascular type device 10 is here described for a C-shaped arm 16. However, in an alternative embodiment, this arm 16 may have other shapes, such as a U shape. Moreover, the lift may be connected to the tube 12. In this case, the detector 13 is directly fixed to the arm 16.

Figure 2:
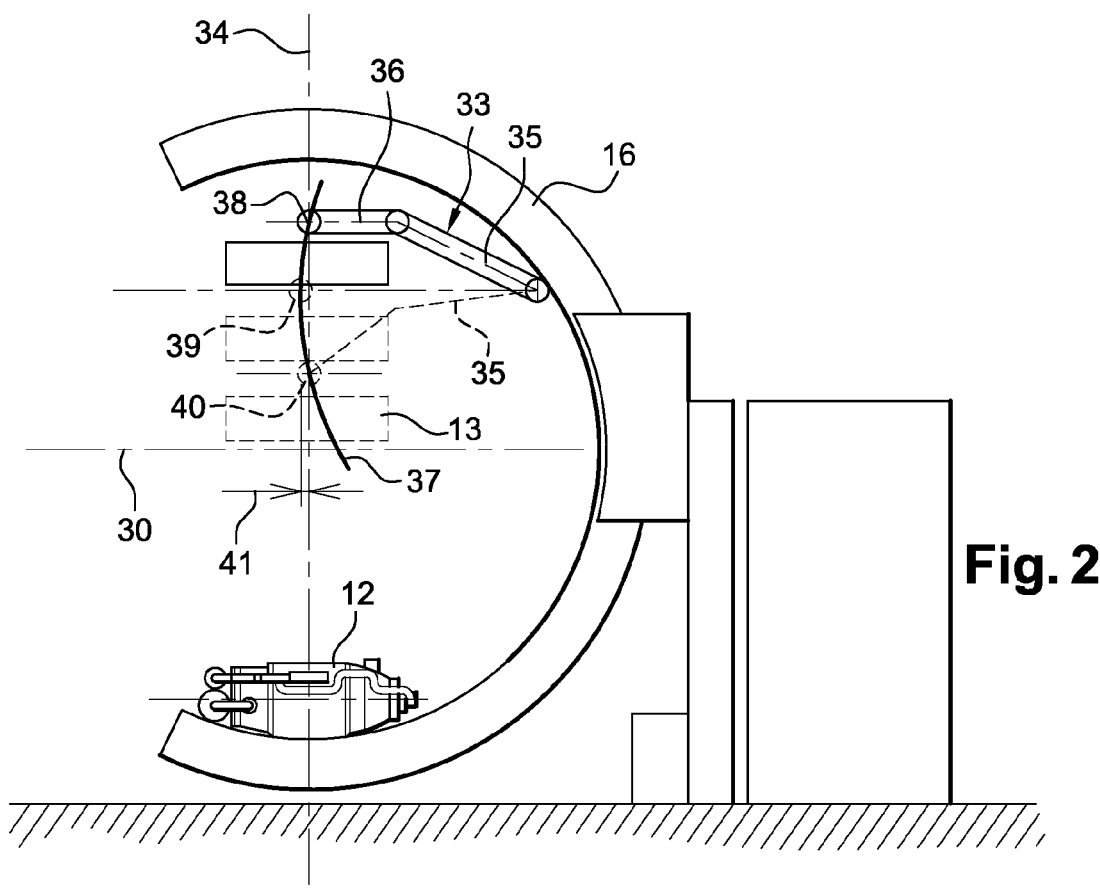
FIG. 2 is a schematic representation of a sectional view of the cradle of the vascular type device, as set forth in an embodiment of the invention.

FIG. 2 shows a sectional view of the cradle of the vascular device, as set forth in the invention. For a radiology device comprising a rotating lift to operate correctly, it is necessary to obtain and maintain, for all the incidence angles, a perfect alignment of the focal point of the X-ray tube, the element observed and the detector with a good accuracy. This geometric imperative is achieved in the invention by means of a compensation system 33.

This compensation system 33 enables the tube 12 or the detector 13 to be kept aligned on an alignment line 34 passing through the focal point, the isocentre of the device and the middle of the detector 13. The isocentre of the tube is a point situated at the intersection of the central axis of the beam and the axis of the rotating or curved movement of the X-ray tube 12. This alignment line 34 is perpendicular to the axis 30, when the arm 16 is at zero degrees.

In a preferred embodiment, the compensation system 33 comprises a cam 35 fitted to a free end of the lift. The cam 35 is a mechanical component intended to transform the rotational movement of the lift into a translational movement. The cam 35 is a cylinder of variable radius driven in rotation by a shaft.

The compensation system 33 comprises a lever 36 in contact on the one hand with the profile of the cam 35. The lever 36 is in contact on the other hand with the detector 13. As soon as the cam 35 is in movement, the lever 36, following, is then brought into translational movement.

In a preferred embodiment, the cam 35 is an exterior profile cam. This type of cam enables a drive thrust to be generated. In this case, when the lift rotates, the cam 35 pushes the lever, which in return pushes the detector to align it with the alignment line 34.

The cam 35 and the lever 36 are brought into contact so that they form a parallelogram. This formation of the cam 35 and the lever 36 enables the detector 13 to be kept in moving trajectory position.

In an alternative embodiment, the compensation system 33 may be formed by at least one pantograph or by pantographs in series. This pantograph is a hinged device, based on the principle of the deformable parallelogram, used to displace the detector 13.

When the lift is in rotation, it follows a circle 37. At each position of the lift, illustrated here by the references 38 to 40, the detector 13 is misaligned with the alignment line 34 by an angle 41. The compensation system 33 of the invention enables this angle 41 to be compensated.

The compensation system 33 of the invention is intended to align the detector or the tube, connected to the lift, to the alignment line 34 at any position of the lift in a sphere. The system 33 enables the use of a flat lift. The fact of reducing in this way the volume of the lift increases the examination angles. Indeed, by reducing the volume of the lift, said lift, even in movement, is always located within the C-shaped arm 16. This enables the C-shaped arm to rotate 360 degrees around the axis 30, thereby increasing the examination angles.

An embodiment of the rotating lift of the invention is a rapid lift with less noise compared to the linear lift of the background art. In one embodiment of the invention, the rotating lift enables an increase in linear speed.

Embodiments of the present invention therefore concern an X-ray device, which includes:

an X-ray tube that emits a beam of X-rays along an emission direction;

an X-ray detector situated in an opposite manner to the emitter and in the emission direction;

an arm that can enter into rotation around an axis of rotation, said arm assuring a displacement of the tube and the detector in the space; and a lift connected to the arm and to the detector or to the tube, the lift being capable of raising and lowering said detector or said tube in an emission direction of the beam of X-rays.

In one embodiment, the lift lowers and raises said detector or said tube with a rotating movement within the arm; and the device includes a compensation system capable of keeping the tube or the detector connected to the lift aligned with an alignment line. During the rotation of the lift, this alignment line passes through a focal point of the tube, an isocentre of the device, and the middle of the detector.

Embodiments of the compensation system may include one or more of the following characteristics:

a cam fitted to a free end of the lift;

a lever in contact with a profile of the cam;

wherein the lever is in contact with the detector or the tube connected to the lift, wherein the cam is an exterior profile cam, wherein the cam and the lever form a parallelogram when brought into contact.

The compensation system can include at least one pantograph or pantographs in series. Additionally, one or more of the following features is implemented in one or more embodiments:

the lift is flat;

the arm rotates 360 degrees around the axis of rotation;

the alignment line is perpendicular to the axis of rotation, when the arm is at zero degrees;

the lift is brought into rotation by an electric motor or by a gear assembly.

This written description uses examples to disclose embodiments of the invention, including the best mode, and also to enable any person skilled in the art to make and use embodiments of the invention.

Although specific features of embodiments of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the scope of the following claims.

The invention claimed is:

1. An X-ray device, comprising:
   an X-ray tube configured to emit a beam of X-rays along an emission direction;
   an X-ray detector situated opposite the X-ray tube and in the emission direction;
   a C-shaped arm configured to enter into rotation around an axis of rotation, the arm assuring a displacement of the X-ray tube and the X-ray detector in space;
   a rotating lift connected to the C-shaped arm and having a rotating movement within the C-shaped arm, wherein the rotating lift has an end connected to the X-ray detector or to the X-ray tube, wherein the rotating movement of the rotating lift raises and lowers the X-ray detector or the X-ray tube in the emission direction; and
   a compensation system coupled to the rotating lift, the compensation system comprising a mechanical component configured to translate the rotating movement of the rotating lift into translational movement,
   wherein the translational movement keeps the X-ray tube or the X-ray detector aligned with an alignment line when the lift rotates within the C-shaped arm, and
   wherein the alignment line passes through a focal point of the tube, an isocentre of the device, and the middle of the detector.

2. The X-ray device of claim 1, wherein the the mechanical component comprises:
   a cam fitted to a free end of the rotating lift; and
   a lever in contact with a profile of the cam, and in contact with the X-ray detector or the X-ray tube.

3. The X-ray device of claim 2, wherein the cam is an exterior profile cam.

4. The X-ray device of claim 2, wherein the cam and the lever form a parallelogram when brought into contact with each other.

5. The X-ray device of claim 2, wherein the cam is configured to generate a drive thrust, wherein the drive thrust is configured to push the lever, and wherein the lever is configured to push the X-ray detector or the X-ray tube to align with the alignment line.

6. The X-ray device of claim 2, wherein the cam comprises a cylinder of variable radius, and wherein the cam is driven in rotation by a shaft.

7. The X-ray device of claim 1, wherein the lift is flat.

8. The X-ray device of claim 1, wherein the C-shaped arm rotates 360 degrees around the axis of rotation.

9. The X-ray device of claim 1, wherein the alignment line is perpendicular to the axis of rotation when the C-shaped arm is at zero degrees.

10. The X-ray device of claim 1, further comprising an electric motor configured to rotate the lift.

* * * * *